United States Patent
Kar et al.

(10) Patent No.: US 8,589,084 B2
(45) Date of Patent: Nov. 19, 2013

(54) DETECTION OF ETHANOL EMISSION FROM A SPARK IGNITION ENGINE OPERATING ON GASOHOLS

(75) Inventors: Kenneth Kar, Belmont, MA (US); Wai K. Cheng, Lexington, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 376 days.

(21) Appl. No.: 12/901,029

(22) Filed: Oct. 8, 2010

(65) Prior Publication Data

US 2012/0089343 A1  Apr. 12, 2012

(51) Int. Cl.
 *G06F 19/00* (2011.01)

(52) U.S. Cl.
 USPC ............. 702/24; 205/281; 205/282; 205/296; 205/288; 60/601; 60/605.1; 123/1 A; 123/528; 123/575; 123/431; 123/478; 123/430

(58) Field of Classification Search
 USPC ................... 702/24; 205/281, 282, 296, 288; 60/601, 605.1; 123/1 A, 528, 540, 575, 123/704, 520, 431, 406.47, 430, 304, 478
 See application file for complete search history.

(56) References Cited

U.S. PATENT DOCUMENTS

| | | | | |
|---|---|---|---|---|
| 5,473,162 A * | 12/1995 | Busch et al. | ............... | 250/341.6 |
| 6,297,499 B1 * | 10/2001 | Fenn | ............... | 250/288 |
| 6,750,448 B2 * | 6/2004 | Turecek et al. | ............... | 250/281 |
| 7,146,802 B2 | 12/2006 | Lee | | |
| 7,264,785 B2 | 9/2007 | Blakeman et al. | | |
| 7,732,378 B2 * | 6/2010 | Thompson et al. | ............ | 506/13 |
| 7,981,680 B2 * | 7/2011 | Cummings | ............ | 436/60 |
| 8,030,611 B2 * | 10/2011 | Kishi et al. | ............ | 250/282 |
| 8,076,635 B2 * | 12/2011 | Geromanos et al. | ......... | 250/281 |
| 8,141,356 B2 * | 3/2012 | Leone et al. | ............ | 60/601 |
| 8,202,730 B2 * | 6/2012 | Cummings | ............ | 436/60 |
| 8,207,495 B2 * | 6/2012 | Mukaibatake et al. | ...... | 250/283 |
| 8,283,626 B2 * | 10/2012 | Brown et al. | ............ | 250/282 |
| 8,288,720 B2 * | 10/2012 | Taniguchi | ............ | 250/290 |
| 2003/0197121 A1 * | 10/2003 | Turecek et al. | ............ | 250/281 |
| 2006/0040256 A1 * | 2/2006 | Caulfield et al. | ............ | 435/4 |
| 2007/0034192 A1 * | 2/2007 | Kamio et al. | ............ | 123/478 |
| 2008/0166697 A1 * | 7/2008 | Caulfield et al. | ............ | 435/4 |
| 2008/0282998 A1 | 11/2008 | Kuzuoka et al. | | |
| 2009/0178654 A1 * | 7/2009 | Leone et al. | ............ | 123/528 |
| 2010/0120158 A1 * | 5/2010 | Cummings | ............ | 436/60 |
| 2011/0226946 A1 * | 9/2011 | Caulfield et al. | ............ | 250/282 |
| 2011/0232365 A1 * | 9/2011 | Cummings | ............ | 73/23.37 |

* cited by examiner

Primary Examiner — Carol S Tsai

(74) Attorney, Agent, or Firm — McCarter & English, LLP

(57) ABSTRACT

Ethanol emissions from a direct ignition spark ignition are measured using mass spectrometry. The method exploits specific fragment ions from ethanol. Ethanol contributes ions of mass number 31, and no other gas species produces ions at this mass number. The method and a device for implementing the method can be used for online detection of ethanol in emissions from engines burning E85 or other ethanol/gasoline mixtures.

26 Claims, 7 Drawing Sheets

DETECTION OF ETHANOL EMISSION FROM A SPARK IGNITION ENGINE OPERATING ON GASOHOLS

BACKGROUND

Ethanol has been increasingly used as a transportation fuel, mostly blended with gasoline. In the US, most gasoline in the market contains 10% ethanol. High concentration blends (E85, 85% ethanol and 15% gasoline by volume) are sold in Brazil, Sweden, and in some states in the US. Other countries are planning to use ethanol.

Compared with gasoline, ethanol has superior anti-knocking properties and its heat of vaporization is about three times as high as gasoline. Both characteristics are highly desirable for direct injection spark ignition engine downsizing strategies which could significantly reduce fuel consumption of vehicles without compromising performance. When an ethanol/gasoline blend is burned in an internal combustion engine, oxygenates are produced as unburned fuel or partial oxidation products. Exhaust gas studies have found that ethanol and acetaldehyde are the main oxygenate species. Acetaldehyde is carcinogenic if inhaled. It is also an ozone precursor which contributes to smog formation. Ethanol in the atmosphere is further oxidized to acetaldehyde, which increases the atmospheric acetaldehyde inventory.

Higher ethanol content in fuel leads to more organic gas emission from an internal combustion engine. At present, the US EPA and CARB emission regulations for E85 requires speciated measurement of ethanol and carbonyls. The dominant carbonyl species is acetaldehyde. The CARB test procedure recommends water impinge sampling followed by gas chromatograph (GC) analysis for ethanol measurements. The carbonyl measurement is performed through acidified 2,4-dinitrophenylhydrazine cartridge sampling and high performance liquid chromatography (HPLC) analysis. These methods are sensitive to very low concentration and free of interference from other species, but require considerable manual handling and lengthy analysis time. Another method for measuring ethanol concentration involves the use of photoacoustic sensors (PAS), which has been approved by CARB as equivalent to the water impinger method. PAS utilizes a much simplified sampling method, and the result is available online, similar to conventional emission analyzers. However, compensation for ammonia and carbon dioxide is required to get an accurate ethanol concentration. Fourier Transform Infra Red Spectroscopy (FTIR) can also be used to detect ethanol and acetaldehyde, but is subject to interference from other species. In summary the challenge for ethanol and acetaldehyde measurements is to isolate these species for analysis from a complex mixture of exhaust gas, which may contain hundreds of components. Chromatography is an effective means to resolve the mixture, but the analytical procedures are relatively complex and time consuming. Attempting to analyze the mixture without separation is quicker but generally has cross interference problems.

In mass spectrometry, a gas mixture is admitted to a high vacuum chamber, where it is ionized. Ions are then separated by their mass-to-charge ratio using various means depending on the type of mass analyzer, e.g. quadrupole, magnetic sector, or time-of-flight. Separating exhaust gas species by mass does not guarantee freedom from interference. For example, ethanol and nitrogen dioxide both have a nominal atomic mass of 46. Similarly, carbon dioxide and acetaldehyde both have an atomic mass of 44. Moreover, during the ionization process a gas molecule can split into smaller fragments, adding another source of interference. To minimize the effect of fragment ions, most mass spectrometers used in exhaust gas analysis utilize chemical ionization. Chemical ionization is a low energy process, which yields fewer fragments. Some methods of detecting ethanol and acetaldehyde have used three different chemical ionization levels, chosen to avoid ionizing interfering species. Nevertheless, ethanol still interfered with acetaldehyde in these methods, requiring compensation.

Thus, there remains a need to develop mass spectrometric methods of detecting ethanol, acetaldehyde, and other components of exhaust gases without interference from other chemical species.

SUMMARY OF THE INVENTION

The invention provides methods and devices for online measurement of chemical components in an exhaust gas. Exhaust gases such as those produced by a spark ignition engine burning an ethanol/gasoline blend, such as E85, for example, can be analyzed by preferred embodiments of the invention to accurately measure exhaust gas components using mass spectrometry.

One aspect of the invention is a method of detecting ethanol in an exhaust gas from a spark ignition engine burning an ethanol/gasoline blend. The method includes the steps of collecting a sample of exhaust gas from a spark ignition engine, ionizing the sample to form a plurality of charged molecular species, separating the plurality of charged molecular species using mass spectrometry, and detecting the charged molecular species. The sample is ionized such that ethanol in the sample forms a charged molecular species having a mass/charge ratio of 31 amu (atomic mass units), which is quantified by mass spectrometry. Preferably the ionization method is electron ionization, and the sample is diluted prior to performing ionization and mass spectrometry. The method avoids having to separate the different molecular species in the exhaust gas sample prior to ionization and determination by mass spectroscopy. The detection of ethanol as its 31 amu fragment assures that there are no interfering molecular species from other components of the exhaust gas emission at significant levels, so that detection of ethanol can be performed quickly and in an online fashion using mass spectrometry alone, i.e., without using an additional separation technique such as gas chromatography. The detection of ionized molecular species having a mass/charge ratio of 31 is indicative of the presence of ethanol in the emission and can be used to determine the concentration of the ethanol in the emission. Related methods can be used to detect other molecular species in the exhaust gas, including acetaldehyde at a mass/charge ratio of 43, benzene at a mass/charge ratio of 78, and toluene at a mass/charge ratio of 92.

Another aspect of the invention is a device for the online determination of ethanol concentration in exhaust gas from a spark ignition engine burning a mixture of ethanol and gasoline. The device includes a sampling port that takes in a sample of the exhaust gas, a mass spectrometer that ionizes the sample to form a plurality of charged molecular species, separates the charged molecular species according to their mass/charge ratio and detects the separated charged molecular species to form a mass spectrum, and an analysis module that analyzes the mass spectrum to determine the ethanol concentration in the exhaust gas. The ionization module of the mass spectrometer forms a charged molecular species from ethanol having a mass/charge ratio of 31 amu, which is detected by the mass spectrometer. Preferably the ionization module performs electron ionization, and the device does not include a mechanism for performing another type of molecular separation, such as gas chromatography. In some embodiments, the device, or part thereof, is portable or handheld.

DETAILED DESCRIPTION OF THE INVENTION

The invention provides a completely new approach to the measurement of combustion products, particularly ethanol, in exhaust gases of spark ignition engines burning ethanol-gasoline mixtures. Instead of attempting to minimize fragments and hence interference from other molecular species, the present invention enables identification of ethanol and other constituents of exhaust gas from their fragment ions. The invention utilizes an ionization process that produces fragment ions which are sufficiently repeatable and unique that they can be used in a mass spectrometry system to quantify certain molecular species in a sample.

This new technique was developed in two stages. In the first stage, exhaust speciation data were obtained from gas chromatography, and the distribution of fragment ions from major organic gas species was investigated. In the second stage, detection schemes from the first stage were validated in an engine experiment.

A mass spectrometer for use with the invention includes an ionization module, a mass filter module, and a detector module. The mass spectrometer employed was a Pfeiffer Omnistar GSD300. It has an oil-free vacuum system (a turbomolecular pump backed by a diaphragm pump) to achieve a hydrocarbon-free background, which is essential for detecting trace organic gases. Gases were ionized by electron impact at 60 eV. The ions were then analyzed by a quadrupole mass filter (Pfeiffer QMS200). While any form of high energy ionization can be used, the ionization energy needs to be at least 60 electron volts (EV) in order to practice a method in accordance with the invention. A lower ionization energy might produce different fragments from ethanol or other molecular species in the sample, leading to different results. A DC voltage and a radio frequency voltage were applied to the four rods. Depending on the combination of DC and AC voltage, ions of only one mass-to-charge ratio (m/z) will pass through the rods and reach the Faraday cup detector. The operator specifies a range of m/z, and the instrument typically will set the DC and AC voltages accordingly. The operating parameters of the mass spectrometer are given in Table 1.

TABLE 1

Operating parameters of Pfeiffer Omnistar mass spectrometer.

| | |
|---|---|
| Ion source | Tungsten filament |
| Filament current | 1 mA |
| Quadrupole rod diameter | 6 mm |
| Quadrupole rod length | 100 mm |
| Mass scan range | 0-50 amu |
| Mass scanning speed | 1 s/amu |
| Resolution, adjustable | 0.5-2.5 amu |
| Peak ratio reproducibility | 0.5% |

Figure 1:
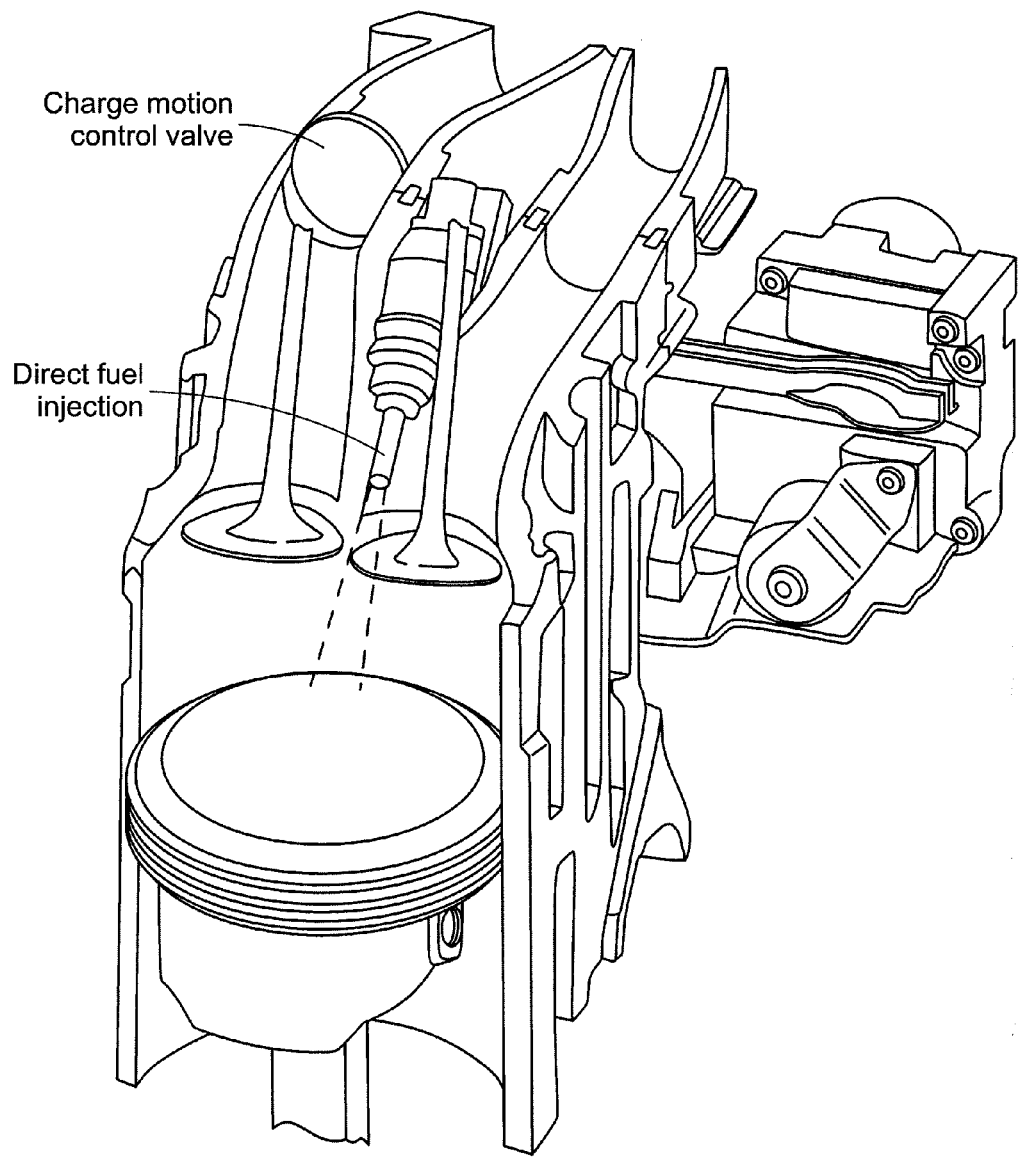
FIG. 1 illustrates the charge motion and injector arrangement of the test engine.

The engine was a GM naturally aspirated DISI Ecotec 4-cylinder engine that was modified for single cylinder operation. Cylinder No. 1 was the only active cylinder, with the intake and exhaust separated from the remaining three cylinders, which were under wide-open-throttle (WOT) motoring operation. The engine was equipped with a charge motion control valve at the intake port to provide a swirling charge motion; see FIG. 1. The valve was closed (swirl-enabled) for all the experiments in this study. The engine specification is shown in Table 2.

TABLE 2

Engine specification.

| | |
|---|---|
| Displacement per cylinder | 550 cc |
| Bore | 86 mm |
| Stroke | 94.6 mm |
| Compression ratio | 12.0 |
| IVO/IVC | 0° after TDC/60° after BDC |
| EVO/EVC | 44.5° before BDC/10.5° after TDC |
| Injector Center Line | 47° from horizontal |
| Nominal cone angle | 52° |
| Injection pressure | 40 to 120 bar |

The engine coolant temperature (ECT) was controlled using a heater in a 80-L coolant tank. To control the injection pressure, the engine fuel pump was not used. Instead, premixed ethanol/gasoline blends were supplied from individual accumulators pressurized by high pressure nitrogen at 70 bar. Other studies on hydrocarbon emission have shown that low and stable emissions are achieved at 70 bar injection pressure. The fuel line was arranged so that the residual fuel could be evacuated by a PTFE dry pump. The flushing process was validated by observing the change in fuel pulse width under stoichiometric conditions when the fuel was switched from gasoline to E85.

A Kistler 6125A piezoelectric pressure transducer with flame arrester and a Kistler 510 charge amplifier were used for in-cylinder pressure measurements. In-cylinder pressure was pegged to the manifold absolute pressure at BDC in the intake stroke.

An emission certification gasoline Haltermann HF473 was used. Its fuel properties are summarized in Table 3. E85 was made by blending anhydrous ethanol (Pharmco-Aaper 200 proof, 99.98% pure) 85% by volume and 15% by volume of Halternann gasoline. The fuel was blended just before it was pumped into the accumulator for testing.

TABLE 3

Haltermann gasoline properties.

| Property | Value | |
|---|---|---|
| Density (ASTM 4052) | 741 | kg/m$^3$ |
| Reid vapor pressure | 62 | kPa |
| Sulfur (by weight) | 28 | ppm |
| Oxygen (by weight) | <0.01 | |
| Hydrogen/Carbon ratio | 1.826 | |
| Lower heating value (ASTM D3338) | 43.04 | MJ/kg |
| Research Octane No. | 97.4 | |
| Motor Octane No. | 89 | |
| Aromatics | 27.1% | liquid vol. |
| Olefins | 0.6% | liquid vol. |
| Saturates | 72.3% | liquid vol. |

Exhaust gas was sampled from a mixing tank 2 m from the exhaust port. This eliminated any spatial and temporal variation of exhaust gas species. The exhaust sample was conveyed to a 1 m fused silica capillary with an internal diameter of 0.15 mm. The response time of the sampling system was about 5 seconds. To avoid condensation in the capillary, the capillary was heated and controlled to 150±1° C. During sampling, the pressure of the vacuum chamber in the mass spectrometer was in the range of $3.5$-$3.7 \times 10^{-6}$ mbar.

A mass spectrometer does not measure gas species concentration directly; it measures ion current at the Faraday cup detector. Therefore, in order to quantify the concentration of a gas species, the mass spectrometer has to be calibrated. A 1000 ppm ethanol mixture (balanced with nitrogen) was created in a 5 L heated cylinder at 70° C. Two absolute pressure transducers (MKS Baratron 629B) were instrumented to measure low (up to 13.3 kPa) and high gas pressure (up to 4000 kPa). The cylinder was initially evacuated, and then 0.11 ml of pure ethanol (Pharmco-Aaper 200 proof) was injected into the cylinder, which resulted in a vapor pressure of 1.050 kPa. The cylinder pressure increased to the measured value as soon as injection was completed. The value remained stable, which indicated that there was no fuel condensation and that the evaporation was complete. Nitrogen of ultra high purity (99.999%) was admitted to the cylinder to just above atmospheric pressure. At this point, the nominal concentration of ethanol was 10,000 ppm which was 10 times higher than the desired pressure. A mechanical fan was used to fully mix the gases for 5 minutes. A second stage dilution was applied by evacuating the cylinder to 10.49 kPa and filling it with nitrogen again to 104.1 kPa. A mechanical fan was used again to mix the gases. This two stage dilution was the key to high accuracy in the final blend. Attempting to create the mixture in one pass would have required very low ethanol pressure at which the limited resolution of the absolute pressure transducer would have led to a large error. The final ethanol concentration was 996.9±5.3 ppm. This error was determined using error of propagation analysis with a 95% confidence interval.

The mass spectrometer sampled the gas mix via a heated capillary inlet (at 150° C.). The ion currents at amu 31, 43, 44, 45 and 46 were recorded. Forty samples were averaged to calculate the gain [ppm/A]. The custom blending of the calibration gas permitted the interference between gases to be studied quickly.

Mass spectrometry does not offer positive identification for a specific species in exhaust gas for several reasons. First, there could be several species present which have identical masses; these would be detected at the same time. Second, in electron impact (EI) ionization, gas molecules are bombarded by a high-energy electron beam (60 eV). A molecule can split into smaller fragments, so a molecule can give a response at masses other than the nominal molecular mass. Third, the mass spectrometer used has a quadrupole mass filter, which differentiates charged molecules by their mass to charge ratio (m/z). A molecule can be charged multiple times in the ionization process, so the mass spectrometer can register responses at m/z=40, 20 and 10 for a gas molecule with amu=40.

Each gas has a mass spectrum that is unique and reproducible, similar to a fingerprint. In GC-MS, a gas mixture is first separated into individual components. The mass spectrum of an unknown component can be identified by comparing the measured mass spectrum to a mass spectrum library. This identification is not possible if a gas mixture is analyzed in the mass spectrometer, as there is no chromatographic separation. Therefore a requirement for successful MS detection is to ensure a peak in a spectrum is only due to one gas component, and nothing else.

Figure 2:
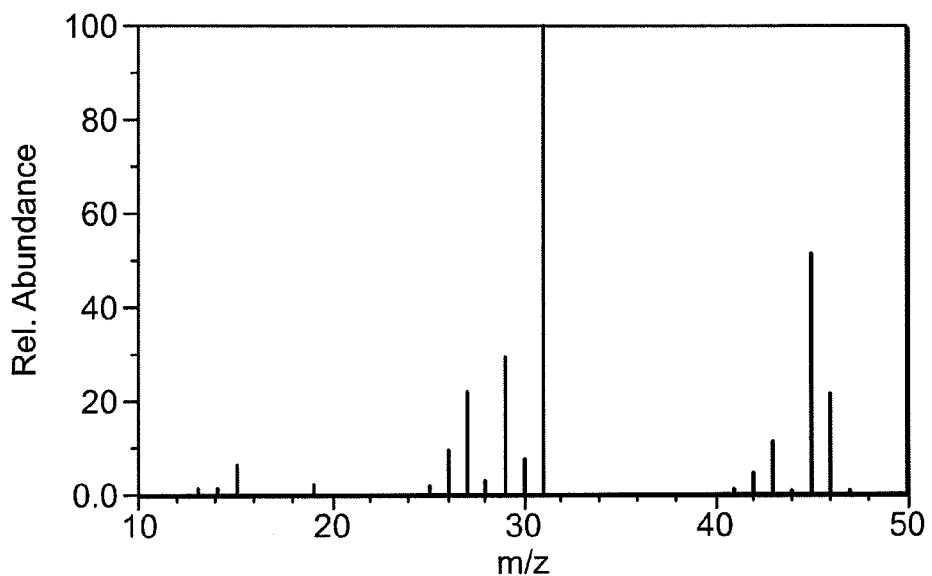
FIG. 2 shows the mass spectrum of ethanol. The ordinate is relative abundance. The most abundant ion is assigned with 100% relative abundance. Other ions are scaled according to the most abundant one.
Figure 3:
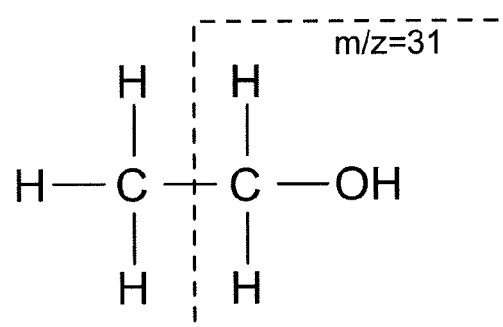
FIG. 3 depicts the most common mode fragmentation of ethanol in the ionization process.
Figure 4:
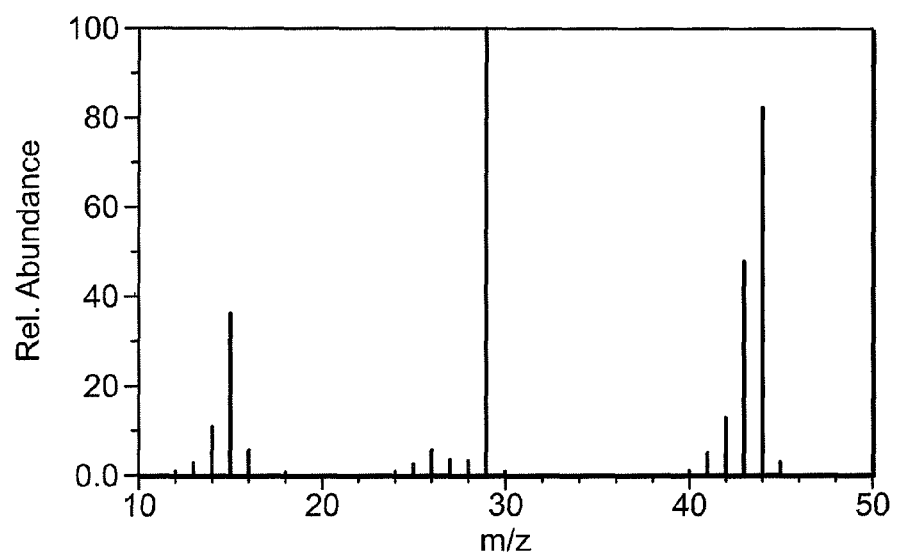
FIG. 4 shows the mass spectrum of acetaldehyde.

The following experiments were carried out to establish that ethanol can be detected without interference from other exhaust gas species. A typical ethanol mass spectrum is given in FIG. 2. The abscissa of FIG. 2 is relative abundance. The ion currents are normalized to that of the most abundant one. Ethanol has a nominal atomic mass of 46, but the ethanol molecular ion is not the most abundant ion. Cleavage of the C—C bond next to the oxygen usually occurs during ionization (see FIG. 3), so that the $CH_2OH^+$ fragment with atomic mass of 31 is the most abundant ion. For acetaldehyde, hydrogen next to the carboxyl group is usually stripped away, yielding $CH_3O^+$. The whole carboxyl group can break off, forming a $CHO^+$ ion. This is why the peaks at m/z=43 and 29 are amongst the highest in the mass spectrum of acetaldehyde (FIG. 4).

A positive detection of either ethanol or acetaldehyde requires that their mass spectra do not overlap with the mass spectrum of other exhaust gas species. For example, it is known that nitrogen dioxide ($NO_2$) can interfere with ethanol, and carbon dioxide can interfere with acetaldehyde. In addition, ethanol and acetaldehyde can interfere with each other, as both species have peaks from m/z=41 to 45. Other hydrocarbons in the exhaust may create fragment ions that overlap with ions produced from ethanol and acetaldehyde. To investigate the extent of interference, an extensive survey of exhaust gas species were conducted. Exhaust gas from the same engine was speciated using gas chromatography. Major organic gas species with concentration no less than 10% of ethanol concentration were selected. Combustion products such as nitrogen dioxide and carbon dioxide were also included in the survey, as their mass spectra cover the range where interference is possible.

The mass spectrum data (relative abundance) of the selected species were obtained from the literature. The survey was restricted to mass numbers 27, 29, 31 and 42 to 46 inclusively. These are the mass numbers where ethanol and acetaldehyde yield the most ions. The results of the survey are summarized in Table 4. First, there is no mass number which has ions coming from a single species. However at m/z=31, ions from ethanol dominate, and contributions from ethane, formaldehyde and acetaldehyde are negligible. It should be noted that Table 4 only gives the relative abundance of ions. The overall effect on the measured concentration is a product of relative abundance and the concentration of an interfering specie. Acetaldehyde and formaldehyde are partial oxidation products of ethanol. Previous research has shown that their mole concentrations are 5-10 times smaller than that of ethanol. Ethane concentration is smaller still ($\frac{1}{7}$ to $\frac{1}{32}$ of ethanol), depending on the ethanol content of the fuel. Therefore, this survey indicated that ethanol can be uniquely detected at mass number 31 for all practical purposes.

Figure 5:
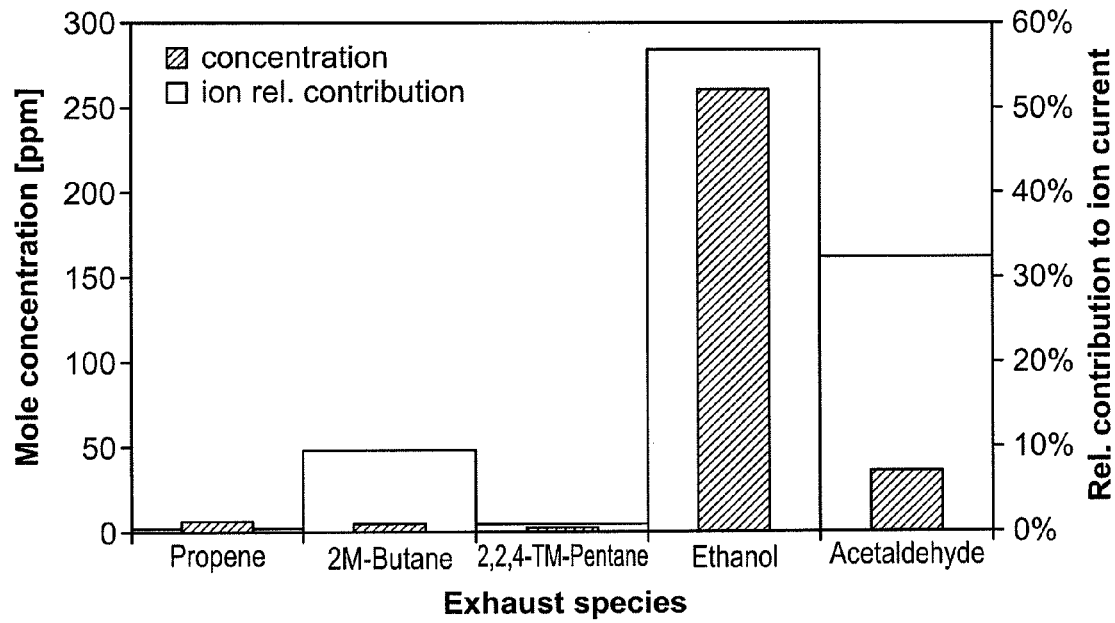
FIG. 5 shows the mole concentration of exhaust species and their relative ion contribution at mass 43. Engine was running at 1500 rpm, 3.8 bar NIMEP, stiochimetric, E85.

Analysis of acetaldehyde by mass spectrometry is more complex. Eight other species contributed ions at mass number 29, and the situation is similar at mass number 42. Mass numbers 43 and 44 have relatively less interference. The four species that interfere with the detection of acetaldehyde at mass number 43 are shown in FIG. 5. The mole concentrations were measured using gas chromatography when the engine was firing at 1500 rpm, 3.8 bar NIMEP fueled with E85. Although 2-methylbutane has very low concentration compared with acetaldehyde, it contributes 10% of the total ion current. This is because 2-methylbutane has the highest relative abundance at mass number 43. In contrast even when ethanol is 6 times more concentrated than acetaldehyde, its ion contribution is modestly higher than that of acetaldehyde. The ion current contributions from propene and 2,2,4-trimethypentane are negligible. A possible detection scheme is to ignore the interference from 2-methylbutane (though it may introduce an error up to 10%), so that the total ion current is due to ethanol and acetaldehyde. Since ethanol concentration can be determined from mass number 31, the ion current due to acetaldehyde at mass 43 can be isolated.

TABLE 4

Relative abundance of selected exhaust gas species.

| Exhaust gas species | Mass to charge ratio (m/z) | | | | | | | |
|---|---|---|---|---|---|---|---|---|
| | 27 | 29 | 31 | 42 | 43 | 44 | 45 | 46 |
| Ethane | 33.23 | 21.52 | 0.5 | 0 | 0 | 0 | 0 | 0 |
| Propene | 38.73 | 0 | 0 | 70.36 | 2.3 | 0.1 | 0 | 0 |
| 2M Butane | 51.34 | 46.75 | 0 | 81.94 | 99.99 | 4.48 | 0 | 0 |
| 2M Propene | 21.72 | 10.91 | 0 | 3.6 | 0.1 | 0 | 0 | 0 |
| Benzene | 2.62 | 0 | 0 | 0 | 0 | 0 | 0 | 0 |
| Toluene | 1.79 | 0 | 0 | 0 | 0.1 | 0.1 | 1.49 | 0.99 |
| 1,2,4 TM Benzene | 5.36 | 0.58 | 0 | 0.15 | 0.09 | 0.35 | 0.11 | 0 |
| 2,2,4 TM Pentane | 5.29 | 8.49 | 0 | 1.29 | 18.49 | 0.6 | 0 | 0 |
| Formaldehyde | 0 | 99.99 | 0.5 | 0 | 0 | 0 | 0 | 0 |
| Carbon dioxide | 0 | 0.1 | 0 | 0 | 0 | 99.99 | 1.2 | 0.4 |
| Nitrogen dioxide | 0 | 0 | 0 | 0 | 0 | 0 | 0 | 37.03 |
| Ethanol | 22.41 | 29.85 | 99.99 | 4.74 | 11.44 | 0.71 | 51.49 | 21.63 |
| Acetaldehyde | 3.59 | 99.99 | 0.3 | 12.79 | 47.49 | 82.59 | 2.79 | 0 |

Figure 6:
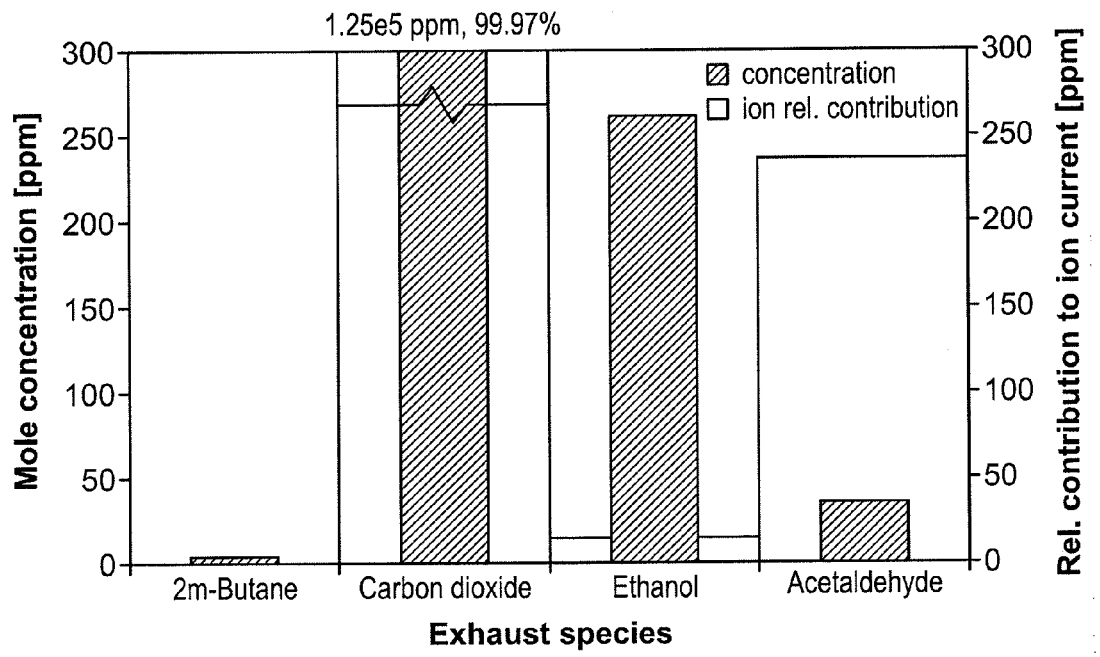
FIG. 6 shows the mole concentration of exhaust species and their relative ion contribution at mass 44. Engine was running at 1500 rpm, 3.8 bar NIMEP, stiochimetric, E85.

Detecting acetaldehyde at mass number 44 is also possible. As shown in FIG. 6, interfering species that are common at both mass numbers 43 and 44 have diminished effect at mass 44 due to smaller relative abundance. For instance, the relative contribution of ethanol to ion current decreases from 57% to 15%. The biggest obstacle is carbon dioxide. Since it is a combustion product, the mole concentration in the exhaust is between 12-13%, depending on ethanol fuel content. This high concentration in effect overshadows acetaldehyde, even though the relative contribution of ion current of acetaldehyde is the highest amongst all organic gases. To successfully detect acetaldehyde at mass number 44, the mass spectrometer must have very high resolution to resolve ion current to ppm level.

Further surveys of exhaust gas components have revealed that additional molecular species can be detected in the exhaust gas of a spark discharge engine burning gasoline or a gasoline/ethanol mixture. These include a variety of compounds containing a phenyl ring, including benzene at a mass/charge ratio of 78 and toluene at a mass/charge ratio of 92. Such ring compounds resist fragmentation during the ionization process, so they can be detected, often without interference from other species, at m/z equal to their molecular weight in amu.

The methods described above were tested in a series of engine experiments. Exhaust gas was sampled to the mass spectrometer in a mixing tank about 2 m from the exhaust port. The capillary inlet was heated to 150° C. to prevent hydrocarbon and water condensation. The vacuum chamber in the mass spectrometer was baked and evacuated for 3-4 hours before the experiment to achieve low background readings. The background mass spectrum only consisted of peaks at 17, 18 and 28 mass numbers. The engine was run with pure gasoline and E85 under idling (1200 rpm, 1.5 bar NIMEP, 15 CAD before TDC ignition timing) and medium load (1500 rpm, 3.8 bar NIMEP, MBT timing). The air/fuel mixture was stoichiometric. Fuel injection occurred in the intake stroke (120 CAD before BDC) to create a homogenous mixture.

Figure 7:
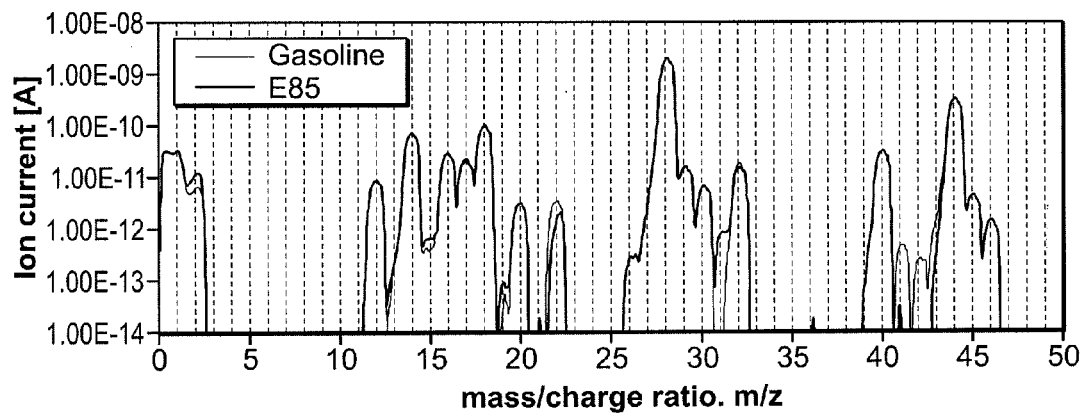
FIG. 7 shows the mass spectrum of exhaust gas when the engine was under idling.
Figure 8:
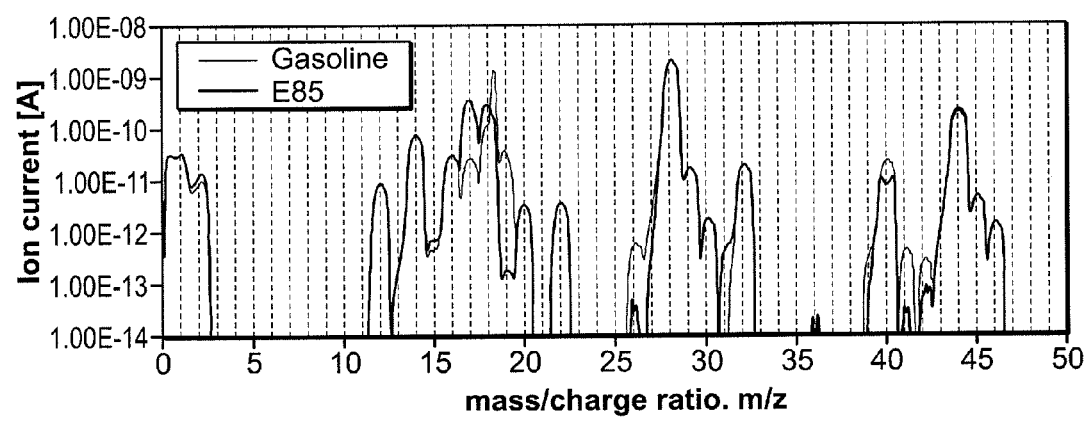
FIG. 8 shows the mass spectrum of exhaust gas when the engine was under idling.

FIGS. 7 and 8 compare the mass spectra of exhaust gas when the engine was fueled with gasoline and E85. Unlike the spectra in FIGS. 1 and 3, these spectra are continuous because they were obtained by incrementally varying the voltages of quadrupole mass filters. A discrete spectrum is usually obtained by reporting the maximum peak ion currents with the corresponding mass numbers. When gasoline was used, the ion current at mass number 31 was lower than $1 \times 10^{-14}$ A, which was near the detection limit. However the ion level increased to the order of $1 \times 10^{-12}$ when the engine switched over to E85. This finding held for both medium load and idling conditions. Therefore the results confirmed that ethanol can be uniquely detected at mass number 31. Ions were detected at mass number 43 in both gasoline and E85, which confirmed that multiple exhaust species contribute ions at mass number 43. Two exhaust species that contributed ions at mass number 43, 2-methylbutane and 2,2,4-trimethylpentane, were found in higher concentration in gasoline exhaust than E85 exhaust. Thus, even though there is no acetaldehyde when gasoline is used, the ion current level is similar to when using E85. Hence acetaldehyde could not be detected exclusively at mass number 43.

The concentration of ethanol is determined by taking the measured ion current at mass number 31 and dividing it by the gain (A/ppm) as determined in calibration. At medium load, there was 290±75 ppm of ethanol in the exhaust gas. The measurement uncertainty includes both the uncertainty in the gain and ion current. It is relatively large because the variation in ion current was 25%. Only 3 mass spectra were recorded, and it is expected that more measurements would increase the precision. Ethanol was measured at 261 ppm using gas chromatography under the same engine conditions (literature value). Since both measurements are comparable, it is concluded that ethanol can be quantified successfully by mass spectroscopy alone using the method of the present invention.

The ion contribution to mass number 43 ($I_{43}$) can be assumed to result predominantly from ethanol and acetaldehyde. Mathematically, it can be expressed as:

$$I_{43} = C_e G_{e,43} + C_a G_{a,43} \quad (1)$$

where, $C_e$ and $C_a$ are the mole concentration of ethanol and acetaldehyde respectively. $G_{e,43}$ is the ion current (gain) at mass number 43 per ppm of ethanol. $G_{a,43}$ is ion current at mass number 43 per ppm (gain) of acetaldehyde. $G_{e,43}$ and $G_{a,43}$ were determined in calibration. $I_{43}$ and $C_e$ are measurements. By rearranging Eq. 1 and making $C_a$ be the subject, the mole concentration of acetaldehyde is determined to be 1550 ppm. This value is 43 times bigger than the gas chromatography measurements (35.8 ppm). This overestimation suggests that there are other ions from other species in mass number 43. Merely removing the interference of ethanol was insufficient in this case. Interference may have resulted also from 2-methylbutane. Another possible explanation is the limited mass resolution of the mass spectrometer. This peak at mass number 44 is large. If the mass spectrometer cannot adequately resolve between mass numbers 43 and 44, $I_{43}$ could register the ions with mass number 44, so it is greatly overestimated. Thus, a mass spectrometer with better resolution would be expected to adequately resolve between mass numbers 43 and 44, making the determination of acetaldehyde concentration more accurate.

For detection and quantification of ethanol and other molecular species of an exhaust gas, the lower limit is determined by the detection limit of the mass spectrometer without averaging the results. For ethanol, the lower limit in these experiments was about 3 ppm. The upper detection and quantification limit for ethanol is about 40,000 ppm, which is a conservative estimate of what the instrument can accommodate. The actual value may be higher, but 40,000 ppm is much higher than what is found in exhaust gas, which generally ranges up to 2000 ppm. Preferably, ethanol is present in the fuel at a concentration in the range from about 2 to 100 volume percent in order for its quantification in the exhaust gas to be carried out by the method. A level of 1.5 volume % of ethanol in gasoline is expected to yield 3 ppm of ethanol in the exhaust, which is approximately the detection limit of the present method.

There are three charged molecular species that can interfere with the detection of ethanol at m/z=31: ethane, acetaldehyde and formaldehyde. The error due to acetaldehyde and formaldehyde is expected to be less than 0.1% with the present method. For ethane, the maximum interference can be estimated using a fuel containing only 1.5% ethanol, where the ethane concentration is estimated at 30 ppm under poor engine running conditions. The error in the measurement of ethanol under such conditions would be 9%. However if the fuel has 10% ethanol, the error reduces to 1%. If 5% error in the measurement is assumed, and the fuel contains only 1.5% ethanol, ethane concentration would be less than 15 ppm. These are extreme conditions, and for most practical purposes the error would be much smaller. For example, if the engine is fully warmed up and running at typical operating conditions, the error due to ethane would be at most about 2%.

There are a few procedures that can be used to enhance the sensitivity of the mass spectrometry. These optional aspects of the method include optimizing the ionization module using air and argon, calibrating the mass scale, and removing any offset error in the electronics. Such procedures are typically documented with the mass spectrometer and are well known. Further, the heating of the sample, for example by using a sample line heated to a temperature above 100° C., for example to about 150° C., can help prevent condensation of water in the sample which can interfere with the performance of the mass spectrometer. Furthermore, a mass spectrometer may take up to 2-3 hours to warm up, stabilize, and achieve a clean background. Thus, it can increase performance to perform a suitable warm-up procedure prior to carrying out the method. A shorter warm-up period such as about 15 minutes can be used, but the measurements will probably be less accurate. The calibration procedure takes about 10 minutes additionally. Once the system has been warmed up, the measurement of an exhaust gas sample can take about one minute to perform. Adequate results can be obtained within about one hour for warm-up, calibration, and measurement of a sample. Exhaust gas contains about 12% water, and water will build up in the mass spectrometer system and needs to be baked out eventually. In one embodiment, the measurement is given one hour per sample so as to limit the amount of water entering the system. Removal of water from the gas to be analyzed can allow the system to run for days continuously without problems.

Figure 9:
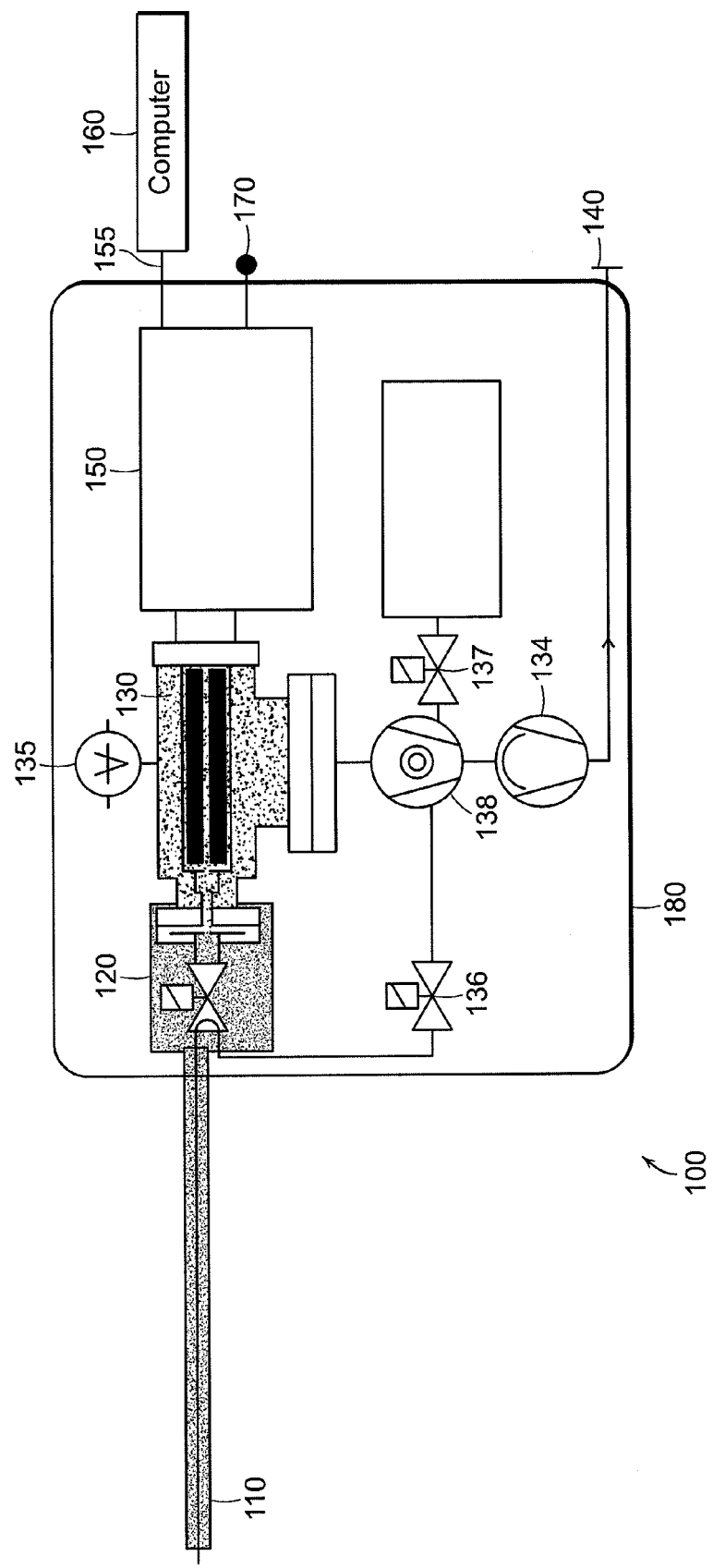
FIG. 9 shows a diagrammatic representation of a device for mass spectrometric analysis of ethanol in exhaust gases.

The invention provides a device for the determination of ethanol or other chemical species in an exhaust gas emission from a spark discharge engine. One embodiment of such a device is depicted in FIG. 9. A sample of exhaust gas is taken up into heated capillary sample line 110 and transported through heated valve and aperture 120 to high vacuum chamber 130. The vacuum in the high vacuum chamber is created using turbomolecular pump 138 in series with diaphragm pump 139. Valves 136 and 137 can be used to adjust the vacuum, and vacuum gauge 135 displays the vacuum level inside the high vacuum chamber. Exhaust port 140 is used to dispose of gas pumped from the high vacuum chamber. After passing through the high vacuum chamber, the sample is taken up by mass spectrometry module 150, which contains an ionization submodule, a mass filter submodule for separation of the charged molecular species according to m/z, and a detection submodule. The results are output via data port 155 to computer 160 for analysis and display. Alternatively, the data can be output via analog port 170 for storage or display on another device. The entire device can be constructed as either a tabletop configuration or as a portable device, and is enclosed in housing 180.

Figure 10:
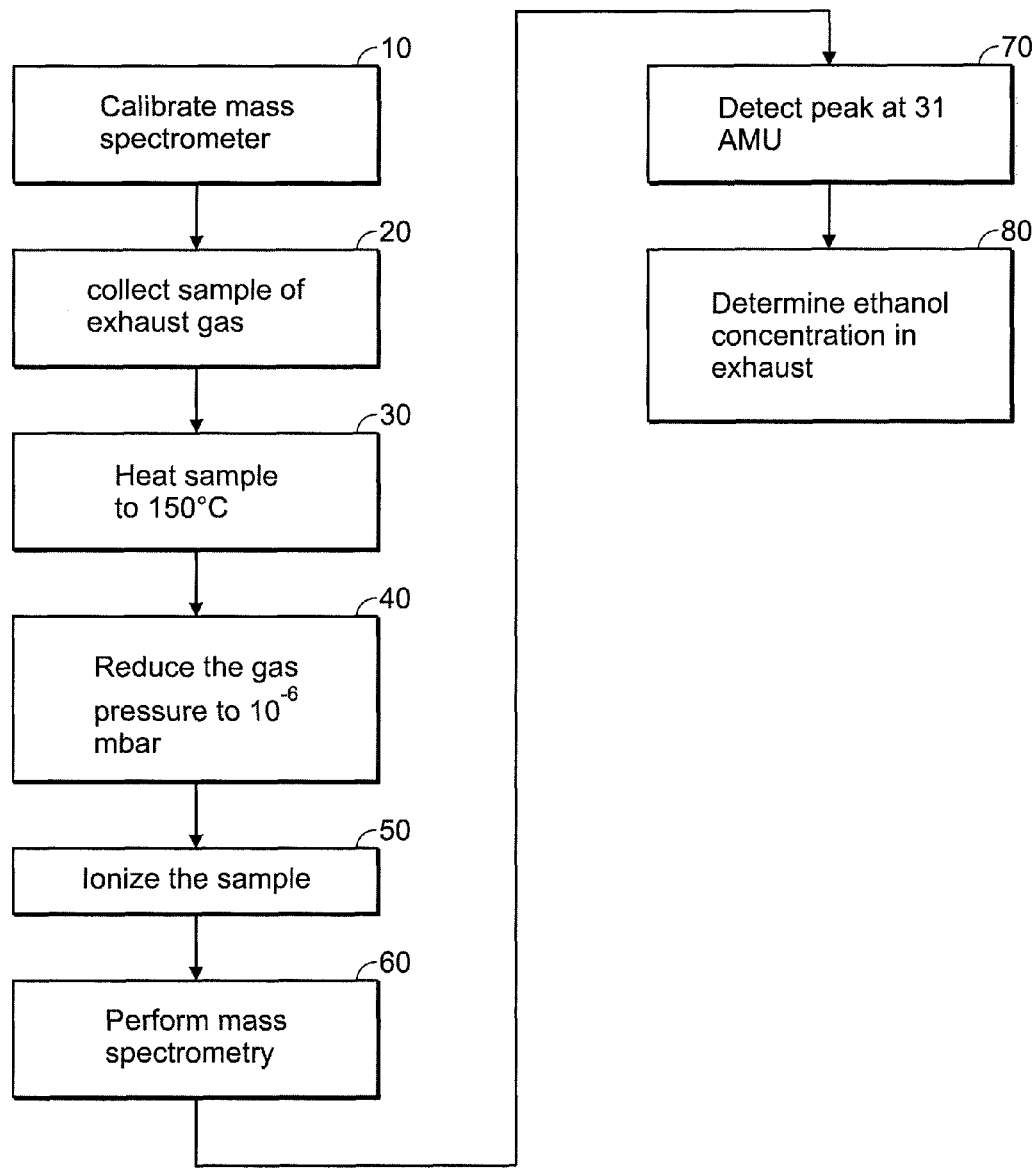
FIG. 10 is a flow chart depicting an embodiment of a method of quantifying the ethanol concentration in vehicle exhaust. The steps shown in gray are performed using a mass spectrometer system.

The invention provides methods for detecting and quantifying certain chemical components of gas emission from a spark discharge engine, including ethanol, acetaldehyde, benzine, and toluene. One embodiment of such a method is summarized in FIG. 10. The first step 10 is the calibration of the mass spectrometer system. This can be accomplished by running one or more samples of gas containing the species to be measured, such as ethanol, in known concentration through the mass spectrometer and observing the amount of signal detected at the relevant m/z value for detection of that species. Typically, several standards are run which cover the expected range of concentrations for the measured species in the emission samples, and a standard curve is established, for example by applying a curve fitting algorithm. The standard samples can be prepared by the user from suitable stocks or purchased from a commercial source. Next, a sample of exhaust gas is collected (20). This can be performed by drawing up a gas sample from a suitable exhaust conduit at the engine or at the tailpipe of a vehicle being tested, for example by applying a vacuum to a sampling port on the measuring device or by using a pump. The sample is preferably heated to about 150 C in order to prevent condensation of water in the sample (30). The gas pressure of the sample is then reduced to about $10^{-6}$ mbar using a vacuum source (40), and the reduced pressure sample is then ionized (50).

Any high energy ionizer can be used that supplies at least 60 electron volts (EV) of ionization energy. Mass spectrometry is then performed on the ionized sample (60), and a suitable peak is detected (70), such as the peak at 31 amu for ethanol. Finally, the ethanol concentration in the exhaust gas sample is calculated (80) using a computer or other microprocessor device that compares the output signal for the peak of interest to the standard curve.

In one method according to the invention, a selected molecular species is detected in an exhaust gas emission from a spark ignition engine. The selected molecular species can be any chemical component of the emission that can be detected based on a peak in a mass spectrum that can be uniquely attributed, in whole or in part, to the selected molecular species. A sample of the emission suspected of containing said selected molecular species is collected and ionized to form a plurality of charged molecular species. During the ionization, the selected molecular species in the sample forms a charged molecular species having a unique mass/charge ratio. The charged molecular species is unique in that at least an approximate correlation can be made between the signal value for the detected peak and the amount of the selected molecular species in the sample. Thus, a known percentage of the signal for the peak of unique mass/charge ratio, such as at least 10%, at least 20%, at least 30%, at least 40%, at least 50%, at least 60%, at least 70%, at least 80%, or at least 90% of the signal is attributable to the selected molecular species or a fragment produced from that species by the ionization process. The plurality of charged molecular species are separated using mass spectrometry to produce a mass spectrum, and the charged molecular species having said unique mass/charge ratio is detected as a means of detecting the selected molecular species in the exhaust gas emission. Preferably, the method does not require or include separation of molecular species in the exhaust gas sample prior to ionization. Detection of the charged molecular species having the unique mass/charge ratio is indicative of the presence of the selected molecular species in the emission, and the signal can be used with an appropriate calibration to quantify the concentration of the selected molecular species in the emission. The method can be applied to the testing of engines or vehicles to ascertain whether or not they pass a test. For example, the method can determine whether the concentration of the selected molecular species in the emission falls below or above a threshold level required by a government agency.

In conclusion, the present invention relates to systems and methods to detect ethanol and other molecular species in exhaust gas using mass spectrometry has been developed. The method utilizes fragment ions of ethanol generated in the ionization process for mass spectrometry. Based on an extensive survey of exhaust species, the inventors predicted that virtually all ions with mass number 31 come from ethanol. Engine exhaust measurements using both pure gasoline and E85 confirmed that ethanol can be uniquely detected in engine exhaust at mass number 31. Furthermore, the measured ethanol concentration was comparable to previous results obtained using gas chromatography. Therefore, it is concluded that this ethanol detection is not subject to interference from other exhaust species, which are often encountered in other online measurement techniques.

That which is claimed is:

1. A method of detecting ethanol in an exhaust gas emission from a spark ignition engine burning an ethanol/gasoline blend, the method comprising the steps of:
    collecting a sample of said emission suspected of containing ethanol;
    ionizing the sample to form a plurality of forming charged molecular species, the ethanol in the sample a charged molecular species having a mass/charge ratio of 31 atomic mass units (amu);
    separating the plurality of charged molecular species using mass spectrometry to produce a mass spectrum; and
    detecting the charged molecular species having a mass/charge ratio of 31 amu to detect ethanol in said exhaust gas emission;
    wherein said method does not include separation of molecular species in the exhaust gas sample prior to ionization; and wherein detection of the charged molecular species having a mass/charge ratio of 31 amu is indicative of the presence of ethanol in the emission.

2. The method of claim 1, wherein the step of ionizing comprises a process applying an energy of at least 60 electron volts.

3. The method of claim 1, wherein the ionization method is electron ionization.

4. The method of claim 1, wherein the charged molecular species formed from ethanol and having a mass/charge ratio of 31 amu is $CH_2OH^+$.

5. The method of claim 1, wherein the mass spectrometry is carried out using a calibrated mass spectrometer.

6. The method of claim 5, wherein the mass spectrometer is calibrated by a method comprising performing mass spectrometry using one or more samples comprising ethanol at a known concentration.

7. The method of claim 5, wherein the concentration of ethanol in the exhaust gas emission is determined.

8. The method of claim 6, wherein the ethanol concentration in the exhaust gas emission is in the range of 3 to 40,000 ppm.

9. The method of claim 1, wherein the ethanol concentration in the fuel is in the range from 2 to 100 volume percent.

10. The method of claim 1, wherein the fuel is E85.

11. The method of claim 1 which determines whether said engine satisfies a CARB standard.

12. The method of claim 1 further comprising a step selected from the group consisting of: heating the sample to above 100 degrees C., optimizing the ionization module using air and argon, calibrating a mass scale of the mass spectrometer, and removing an electronics offset error in the mass spectrometer.

13. The method of claim 1 that can be carried out in less than about 1 hour.

14. The method of claim 13 that can be carried out in about 1 minute.

15. A device for determination of ethanol concentration in exhaust gas from a spark ignition engine burning a mixture of ethanol and gasoline, the device comprising:
    a sampling port adapted to intake a sample of said exhaust gas;
    a mass spectrometer that ionizes the sample to produce charged molecular species, separates the charged molecular species according to mass/charge ratio, and detects the separated charged molecular species to form a mass spectrum, wherein said mass spectrum includes a feature representing the amount of a molecular species with mass/charge ratio of 31; and
    an analysis module that calculates said ethanol concentration from the mass spectrum feature having a mass/charge ratio of 31 during an exhaust gas measurement.

16. The device of claim 15, further comprising a sample line between said sampling port and said mass spectrometer, wherein the sample line heats the sample to above 100 degrees C.

17. The device of claim 15, wherein the mass spectrometer comprises a turbomolecular pump, a diaphragm pump, and a set of valves to reduce the gas pressure to $10^{-5}$-$10^{-6}$ mbar.

18. The device of claim 15, further comprising a vacuum input line that supplies vacuum to said mass spectrometer.

19. The device of claim 15 which does not separate the sample into different molecular species prior to ionization.

20. The device of claim 15, wherein the analysis module comprises a program that calculates the ethanol concentration of the exhaust gas using a standard curve relating ethanol concentration to relative abundance of the mass spectrum feature having a mass/charge ratio of 31 amu.

21. The device of claim 15 which comprises a portable unit housing at least one of said sampling port, mass spectrometer, and analysis module.

22. A method of detecting acetaldehyde in an exhaust gas emission from a spark ignition engine burning an ethanol/gasoline blend, the method comprising the steps of:

collecting a sample of said emission;

ionizing the sample to form a plurality of charged molecular species, whereby acetaldehyde in the sample forms a charged molecular species having a mass/charge ratio of 43 atomic mass units (amu);

separating the plurality of charged molecular species using mass spectrometry to produce a mass spectrum; and detecting the charged molecular species having a mass/charge ratio of 43 amu to detect acetaldehyde in said exhaust gas emission;

wherein said method does not include separation of molecular species in the exhaust gas sample prior to ionization; and wherein detection of the charged molecular species having a mass/charge ratio of 43 amu indicates that acetaldehyde is present in the emission.

23. A method of detecting benzene in an exhaust gas emission from a spark ignition engine burning an ethanol/gasoline blend, the method comprising the steps of:

collecting a sample of said emission suspected of containing benzene;

ionizing the sample to form a plurality of charged molecular species, whereby benzene in the sample forms a charged molecular species having a mass/charge ratio of 78 atomic mass units (amu);

separating the plurality of charged molecular species using mass spectrometry to produce a mass spectrum; and detecting the charged molecular species having a mass/charge ratio of 78 amu to detect benzene in said exhaust gas emission;

wherein said method does not include separation of molecular species in the exhaust gas sample prior to ionization; and wherein detection of the charged molecular species having a mass/charge ratio of 78 amu is indicative of the presence of benzene in the emission.

24. A method of detecting toluene in an exhaust gas emission from a spark ignition engine burning an ethanol/gasoline blend, the method comprising the steps of:

collecting a sample of said emission suspected of containing toluene;

ionizing the sample to form a plurality of charged molecular species, whereby toluene in the sample forms a charged molecular species having a mass/charge ratio of 92 atomic mass units (amu);

separating the plurality of charged molecular species using mass spectrometry to produce a mass spectrum; and detecting the charged molecular species having a mass/charge ratio of 92 amu to detect toluene in said exhaust gas emission;

wherein said method does not include separation of molecular species in the exhaust gas sample prior to ionization; and wherein detection of the charged molecular species having a mass/charge ratio of 92 amu indicates that toluene is present in the emission.

25. A method of detecting a selected molecular species in an exhaust gas emission from a spark ignition engine, the method comprising the steps of:

collecting a sample of said emission;

ionizing the sample to form a plurality of charged molecular species, whereby said selected molecular species in the sample forms a charged molecular species having a mass/charge ratio;

separating the plurality of charged molecular species using mass spectrometry to produce a mass spectrum; and detecting the charged molecular species having said mass/charge ratio to detect the selected molecular species in said exhaust gas emission;

wherein said method does not include separation of molecular species in the exhaust gas sample prior to ionization; and wherein detection of the charged molecular species having said mass/charge ratio indicates that the selected molecular species is present in the emission.

26. A method of detecting ethanol in an exhaust gas emission from an engine, the method comprising the steps of:

collecting a sample of said emission;

ionizing the sample to form a plurality of charged molecular species, whereby ethanol in the sample forms a charged molecular species having a mass/charge ratio of 31 atomic mass units (amu);

separating the plurality of charged molecular species using mass spectrometry to produce a mass spectrum; and detecting the charged molecular species having a mass/charge ratio of 31 amu to detect ethanol in said exhaust gas emission.

* * * * *